(12) United States Patent
Eaton et al.

(10) Patent No.: US 7,384,604 B2
(45) Date of Patent: Jun. 10, 2008

(54) SAMPLE INTRODUCTION SYSTEM

(75) Inventors: Andrew Eaton, Altrincham (GB);
Andrew Entwistle, Stretford (GB);
Howard Read, Higher Baguley (GB);
Fadi Abou-Shakra, Sale (GB)

(73) Assignee: Micromass UK Limited, Manchester (GB)

( * ) Notice: Subject to any disclaimer, the term of this patent is extended or adjusted under 35 U.S.C. 154(b) by 778 days.

(21) Appl. No.: 10/285,509

(22) Filed: Nov. 1, 2002

(65) Prior Publication Data
US 2003/0109061 A1 Jun. 12, 2003

(30) Foreign Application Priority Data
Nov. 1, 2001 (GB) .................. 0126260.9
Dec. 14, 2001 (GB) .................. 0129967.6

(51) Int. Cl.
*B01L 3/02* (2006.01)
(52) U.S. Cl. .................. 422/100; 422/63; 422/65; 436/180; 73/864; 73/863.32; 73/863.01; 73/864.11; 700/254
(58) Field of Classification Search ................ 422/100, 422/63, 65; 436/180; 73/863.31, 863.32, 73/863.33, 864, 864.01, 864.02, 864.11, 864.17; 700/254
See application file for complete search history.

(56) References Cited

U.S. PATENT DOCUMENTS

| | | | | |
|---|---|---|---|---|
| 4,042,338 A * | 8/1977 | Huber | .................. | 422/64 |
| 4,104,026 A * | 8/1978 | Brooker et al. | ............. | 436/541 |
| 4,259,573 A | 3/1981 | Prober et al. | | |
| 4,349,510 A * | 9/1982 | Kolehmainen et al. | ....... | 422/66 |
| 4,578,244 A * | 3/1986 | Cosgrove et al. | ............. | 422/65 |
| 4,754,414 A * | 6/1988 | Gocho | .................. | 702/31 |
| 5,240,681 A * | 8/1993 | O'Lear et al. | ................ | 422/82 |
| 5,316,726 A * | 5/1994 | Babson et al. | ................ | 422/65 |
| 5,439,569 A * | 8/1995 | Carpio | .................. | 134/1.3 |
| 5,492,831 A * | 2/1996 | Ranger | .................. | 436/50 |
| 5,646,046 A * | 7/1997 | Fischer et al. | ................ | 436/49 |
| 5,695,719 A * | 12/1997 | Lynggaard et al. | ........... | 422/81 |
| 5,709,539 A | 1/1998 | Hammer et al. | | |
| 5,723,861 A | 3/1998 | Carnahan et al. | | |
| 5,801,820 A | 9/1998 | Bysouth et al. | | |
| 6,039,211 A * | 3/2000 | Slater et al. | .................. | 222/1 |
| 6,165,778 A * | 12/2000 | Kedar | .................. | 435/289.1 |
| 6,216,918 B1* | 4/2001 | Saveliev et al. | ............. | 222/148 |
| 6,584,832 B2* | 7/2003 | Petro et al. | ................ | 73/61.52 |
| RE38,281 E * | 10/2003 | Tisone | .................. | 422/100 |
| 6,693,298 B2* | 2/2004 | Eisenbeiser et al. | ........... | 257/63 |
| 6,740,529 B2* | 5/2004 | Takahashi et al. | ........... | 436/179 |
| 6,902,703 B2* | 6/2005 | Marquiss et al. | ........... | 422/100 |
| 7,198,753 B1* | 4/2007 | Campbell et al. | ........... | 422/68.1 |
| 2002/0064880 A1* | 5/2002 | Merten et al. | ................ | 436/43 |

(Continued)

FOREIGN PATENT DOCUMENTS

EP 0 81 116 6/1983

(Continued)

*Primary Examiner*—Brian R. Gordon
(74) *Attorney, Agent, or Firm*—Diederiks & Whitelaw, PLC

(57) ABSTRACT

A sample introduction system includes at least two, and preferably three, syringe pumps. The flow rates of two of the syringe pumps are varied, while keeping the overall flow rate constant. The sample introduction system is preferably utilized in an analytical instrument, such as to determine the concentration of an analyte in a sample.

15 Claims, 6 Drawing Sheets

U.S. PATENT DOCUMENTS

| | | |
|---|---|---|
| 2002/0192113 A1* | 12/2002 | Uffenheimer et al. .......... 422/67 |
| 2003/0129090 A1* | 7/2003 | Farrell ....................... 422/68.1 |
| 2003/0170145 A1* | 9/2003 | Smith et al. ............... 422/68.1 |
| 2003/0215957 A1* | 11/2003 | Lemmo et al. ............. 436/180 |
| 2004/0072364 A1* | 4/2004 | Tisone et al. ............... 436/180 |
| 2004/0219688 A1* | 11/2004 | Churchill et al. ........... 436/180 |
| 2004/0247489 A1* | 12/2004 | Fernando et al. ........... 422/100 |
| 2006/0051247 A1* | 3/2006 | Micklash et al. ........... 422/100 |
| 2006/0133966 A1* | 6/2006 | DiGianfilippo et al. ..... 422/100 |
| 2007/0031294 A1* | 2/2007 | Gaillard et al. ............. 422/100 |

FOREIGN PATENT DOCUMENTS

| | | |
|---|---|---|
| EP | 0107333 | 5/1984 |
| EP | 0 528 386 A2 | 2/1993 |
| EP | 0 684 470 A2 | 11/1995 |
| WO | WO 88/07668 | 10/1988 |

* cited by examiner

SAMPLE INTRODUCTION SYSTEM

BACKGROUND OF THE INVENTION

1. Field of the Invention

The present invention relates to a sample introduction system.

2. Discussion of the Prior Art

Conventional approaches to quantifying the unknown concentration of one or more analytes of interest in a sample using an analytical instrument such as a mass spectrometer (especially Inductively Coupled Plasma ("ICP") mass spectrometers) rely upon having first calibrated the analytical instrument using different strength calibration solutions of an analyte(s) of interest. These calibration solutions are individually prepared off-line which is time consuming and may potentially give rise to inaccuracies. Once the analytical instrument has been calibrated then the concentration of one or more analytes of interest in a sample can be determined by measuring the response of the analytical instrument and comparing the measured response with a calibration curve obtained from measuring the response of the analytical instrument to the various calibration solutions.

The conventional approach is prone to suffering from variations in response due to either differences between the sample matrix and the calibration standards, instrumental drift or combination of the two. These variations in response can be particularly acute with ICP mass spectrometers and therefore being able to determine accurately the concentration of an analyte in an analytical instrument such as an ICP mass spectrometer is a non-trivial matter.

It is therefore desired to be provide an improved method and apparatus for determining the concentration of an analyte(s) in a sample.

SUMMARY OF THE INVENTION

According to a first aspect of the present invention there is provided a sample introduction system for an analytical instrument comprising:

a first fluid dispensing device for dispensing a first fluid comprising a sample with an unknown concentration $C_s$ of an analyte of interest at a sample flow rate $V_s$;

a second fluid dispensing device for dispensing a second fluid comprising a calibration solution with a known concentration $C_c$ of the analyte of interest at a calibration solution flow rate $V_c$;

a third fluid dispensing device for dispensing a third fluid comprising a diluent at a diluent flow rate $V_d$; and control means for automatically varying the calibration solution and diluent flow rates.

An advantage of the preferred embodiment is that the sample is spiked with an internal standard and matrix matched calibration is used.

The preferred embodiment enables rapid automated standard addition and/or isotope dilution calibration to be carried out to determine accurately the level of an analyte(s) in a sample.

The control means is preferably arranged to vary the calibration solution and diluent flow rates whilst maintaining the sum of the sample flow rate, the calibration solution flow rate and the diluent flow rate at a substantially constant value V.

The control means may increase the calibration solution flow rate and decrease the diluent flow rate either in a stepped or continuous manner. Alternatively, the control means may decrease the calibration solution flow rate and increase the diluent flow rate either in a stepped or continuous manner.

The sample introduction system may comprise a mixing device for mixing first fluid dispensed from the first dispensing device with third fluid dispensed from the third dispensing device. A further mixing device for mixing a mixture of first and third fluids with second fluid dispensed from the second dispensing device may also be provided.

The diluent preferably has substantially a 0% concentration of the analyte of interest.

The first, second and third dispensing devices preferably comprise syringe pumps.

The sample introduction system is preferably arranged to introduce a sample to an ion source of a mass spectrometer.

According to a second aspect of the present invention, there is provided an analytical instrument in combination with a sample introduction system. The analytical instrument may comprise either an Inductively Coupled Plasma ("ICP") mass spectrometer, an Inductively Coupled Plasma optical analyser, a flame spectrophotometer, an Atmospheric Pressure Chemical Ionisation ("APCI") mass spectrometer or an Electrospray Ionisation ("ESI") mass spectrometer.

According to a third aspect of the present invention, there is provided a method of determining the concentration of an analyte in a sample, comprising the steps of:

introducing a sample with an unknown concentration $C_s$ of an analyte of interest at a sample flow rate $V_s$ into a sample introduction system;

introducing a calibration solution with a known concentration $C_c$ of the analyte of interest at a calibration solution flow rate $V_c$ into the introduction system;

introducing a diluent at a diluent flow rate $V_d$ into the sample introduction system; and automatically varying the calibration solution and diluent flow rates.

The sample and the diluent may be analysed when the sample and the diluent are being introduced into the sample introduction system substantially without any calibration solution being introduced into the sample introduction system and the sum of the sample flow rate and the diluent flow rate substantially equals the constant value V.

First, second, third and fourth mixtures of the sample, the diluent and the calibration solution may be analysed when the diluent is being introduced into the sample introduction system at a various diluent flow rates and the calibration solution is being introduced into the sample introduction system at various calibration solution flow rates.

According to a bracketing embodiment the method further comprises the steps of:

analysing a mixture of the sample, the calibration solution and the diluent when the calibration solution is being introduced into the sample introduction system at a predetermined flow rate; then analysing a mixture of the sample, the calibration solution and the diluent when the calibration solution is being introduced into the sample introduction system at a flow rate greater than the predetermined flow rate; then analysing a mixture of the sample, the calibration solution and the diluent when the calibration solution is being introduced into the sample introduction system at a flow rate lesser than the predetermined flow rate.

According to another bracketing embodiment the method further comprises the steps of:

analysing a mixture of the sample, the calibration solution and the diluent when the calibration solution is being introduced into the sample introduction system at a predetermined flow rate; then analysing a mixture of the sample, the calibration solution and the diluent when the calibration solution is being introduced into the sample introduction system at a flow rate lesser than the predetermined flow rate; then analysing a mixture of the sample, the calibration solution and the diluent when the calibration solution is being introduced into the sample introduction system at a flow rate greater than the predetermined flow rate.

According to a fourth aspect of the present invention there is provided a sample introduction system for an analytical instrument comprising:

a first fluid dispensing device for dispensing a first fluid comprising a sample with an unknown concentration $C_s$ of an analyte of interest at a sample flow rate $V_s$;

a second fluid dispensing device for dispensing a second fluid comprising a calibration solution with a known concentration $C_c$ of the analyte of interest at a calibration solution flow rate $V_c$; and control means for automatically varying the sample and calibration solution flow rates.

Preferably, the control means is arranged to vary the sample and calibration solution flow rates whilst maintaining the sum of the sample flow rate and the calibration solution flow rate at a substantially constant value V.

The control means may decrease the sample flow rate and increase the calibration solution flow rate in either a stepped or a continuous manner. Alternatively, the control means may increase the sample flow rate and decrease the calibration solution flow rate in either a stepped or a continuous manner.

A mixing device may be provided for mixing first fluid dispensed from the first dispensing device with second fluid dispensed from the second dispensing device.

The first and second dispensing devices preferably comprise syringe pumps.

Preferably, the sample introduction system is arranged to introduce a sample to an ion source of a mass spectrometer.

According to a fifth aspect of the present invention there is provided an analytical instrument in combination with a sample introduction system. The analytical instrument may comprise an Inductively Coupled Plasma ("ICP") mass spectrometer, an Inductively Coupled Plasma optical analyser, a flame spectrophotometer, an Atmospheric Pressure Chemical Ionisation ("APCI") mass spectrometer or an Electrospray Ionisation ("ESI") mass spectrometer.

According to a sixth aspect of the present invention there is provided a method of determining the concentration of an analyte in a sample, comprising the steps of:

introducing a sample with an unknown concentration $C_s$ of an analyte of interest at a sample flow rate $V_s$ into a sample introduction system;

introducing a calibration solution with a known concentration $C_c$ of the analyte of interest at a calibration solution flow rate $V_c$ into the sample introduction system; and automatically varying the sample and calibration solution flow rates.

A blank solution of e.g. pure water is preferably introduced into the sample introduction system and analysed at a flow rate which substantially equals the constant value V substantially without any sample or any calibration solution being introduced into the sample introduction system.

The calibration solution is also preferably introduced into the sample introduction system and analysed at a flow rate which substantially equals the constant value V substantially without any sample being introduced into the sample introduction system.

Similarly, first, second, third and fourth mixtures of the sample and the calibration solution are preferably analysed when the sample is being introduced into the sample introduction system at various sample flow rates and the calibration solution is introduced into the sample introduction system at various calibration solution flow rates.

The sample flow rate is preferably decreased and the calibration solution flow rate is preferably increased or vice versa. The flow rates may be either decreased/increased in steps or in a substantially continuous manner.

A bracketing embodiment is contemplated comprising the steps of:

analysing a mixture of the sample and the calibration solution when the calibration solution is being introduced into the sample introduction system at a predetermined flow rate; then analysing a mixture of the sample and the calibration solution when the calibration solution is being introduced into the sample introduction system at a flow rate greater than the predetermined flow rate; then analysing a mixture of the sample and the calibration solution when the calibration solution is being introduced into the sample introduction system at a flow rate lesser than the predetermined flow rate.

An alternative bracketing embodiment is contemplated comprising the steps of:

analysing a mixture of the sample and the calibration solution when the calibration solution is being introduced into the sample introduction system at a predetermined flow rate; then analysing a mixture of the sample and the calibration solution when the calibration solution is being introduced into the sample introduction system at a flow rate lesser than the predetermined flow rate; then analysing a mixture of the sample and the calibration solution when the calibration solution is being introduced into the sample introduction system at a flow rate greater than the predetermined flow rate.

According to a seventh aspect of the present invention there is provided a method of determining the concentration of an element in a sample, comprising the steps of:

automatically dispensing a sample having an unknown concentration of at least two isotopes of an element of interest into a sample introduction system;

automatically dispensing a solution having at least two isotopes of the element of interest into the sample introduction system;

mixing the sample and the solution in the sample introduction system; and passing a mixture of the sample and the solution to a mass spectrometer downstream of the sample introduction system.

Preferably, the method further comprises the step of:

mass analysing the sample;

determining the intensity of the at least two isotopes present in the sample;

mass analysing the solution;

determining the intensity of the at least two isotopes present in the solution;

mass analysing the mixture;

determining the intensity of the at least two isotopes present in the mixture; and determining the concentration of the element in the sample.

The mass spectrometer preferably comprises an Inductively Coupled Plasma ("ICP") mass spectrometer.

According to an eighth aspect of the present invention there is provided apparatus comprising a sample introduction system for a mass spectrometer and a mass spectrometer arranged downstream of the sample introduction system, the sample introduction system comprising:

a first dispensing device for automatically dispensing a sample having an unknown concentration of at least two isotopes of an element of interest;

a second dispensing device for automatically dispensing a solution having at least two isotopes of the element of interest; and a mixing device for mixing the sample and the solution; wherein the mass spectrometer is arranged to receive a mixture of the sample and the solution from the sample introduction system.

Preferably, the mass spectrometer in a mode of operation:

mass analyses the sample and determines the intensity of the at least two isotopes present in the sample;

mass analyses the solution and determines the intensity of the at least two isotopes present in the solution;

mass analyses the mixture and determines the intensity of the at least two isotopes present in the mixture; and determines the concentration of the element in the sample.

Preferably, the mass spectrometer comprises an Inductively Coupled Plasma ("ICP") mass spectrometer.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
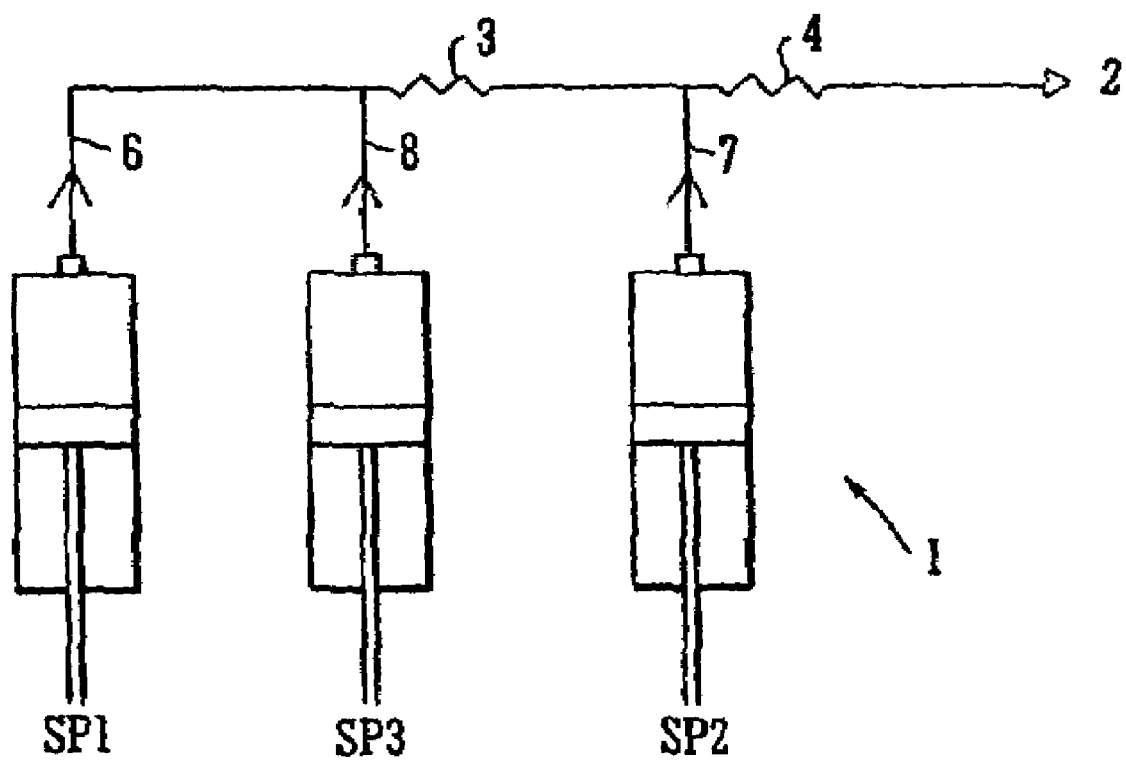
FIG. 1 shows a sample introduction system according to one embodiment of the present invention.
Figure 2A:
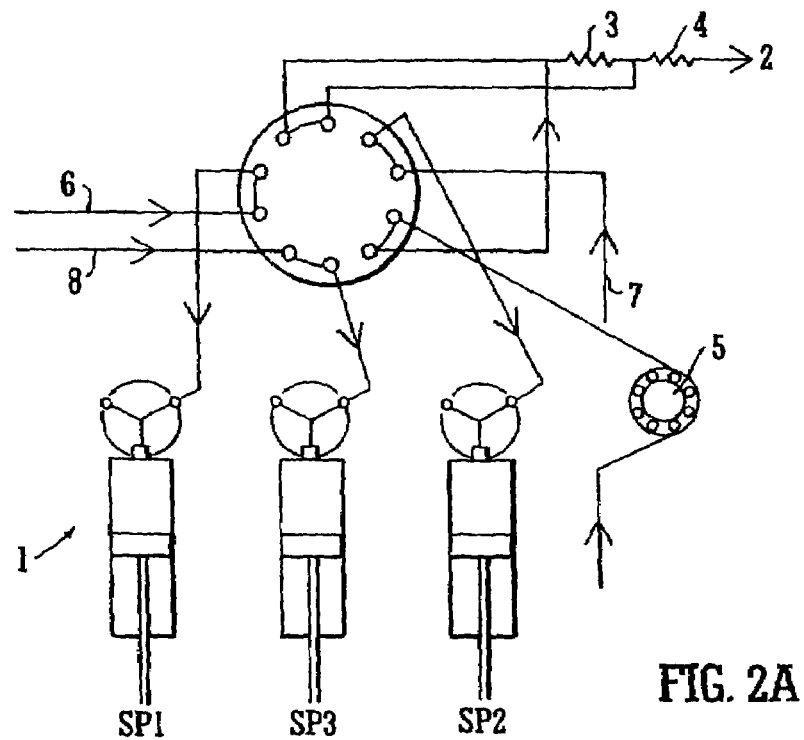
FIG. 2(a) shows a preferred sample introduction system in fill mode.
Figure 2B:
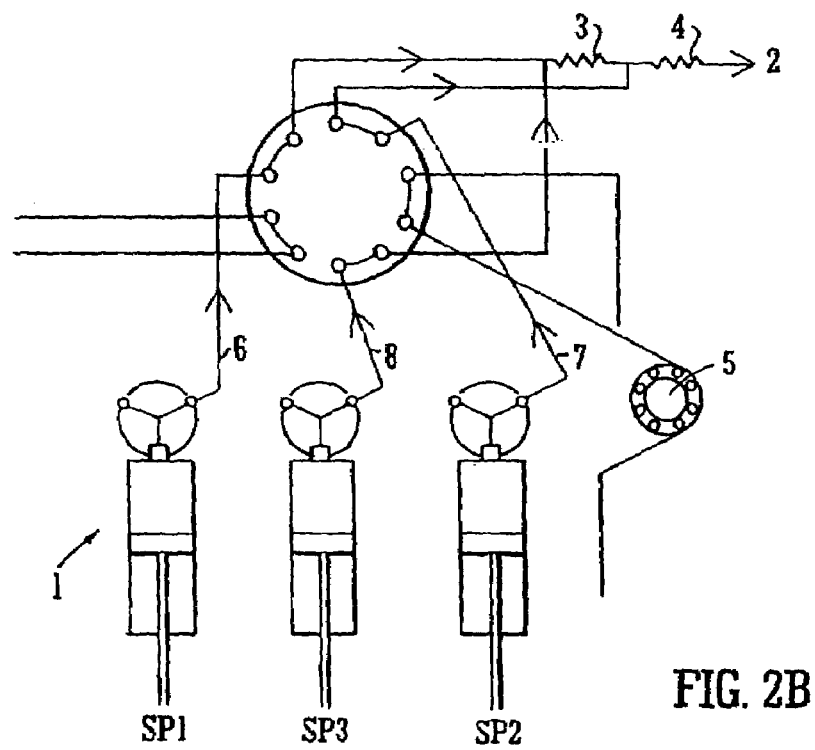
FIG. 2(b) shows a preferred sample introduction system in delivery mode.

A sample introduction system 1 is shown in FIG. 1 and a preferred sample introduction system 1 is shown in FIGS. 2(a) and 2(b). The sample introduction system 1 is arranged upstream of an analytical instrument 2 such as an Inductively Coupled Plasma ("ICP") mass spectrometer.

First, second and third syringe pumps SP1,SP2,SP3 are shown. The first syringe pump SP1 is preferably used to deliver a sample solution 6 and the third syringe pump SP3 is preferably used to deliver an appropriate diluent 8. The sample solution 6 and diluent 8 are preferably mixed in a first mixing coil 3.

The second syringe pump SP2 is used to deliver a calibration solution 7 (or "spike") having a known concentration of an analyte of interest. The calibration solution 7 is preferably mixed with a mixture of sample solution 6 and diluent 8 emerging from the first mixing coil 3 in a second mixing coil 4 downstream of the first mixing coil 3.

The mixture of sample solution 6 and/or diluent 8 and/or calibration solution 7 is then passed to the input of an analytical instrument 2 such as an ICP mass spectrometer.

According to another unillustrated embodiment the diluent syringe pump SP3 and the calibration solution syringe pump SP2 may be arranged so that diluent 8 and calibration solution 7 mix in the first mixing coil 3 and the sample solution 6 is introduced downstream of the first mixing coil 3, preferably so that the mixture of diluent 8 and calibration solution 7 is mixed with the sample solution in the second mixing coil 4.

According to a method of operation, initially the second (calibration solution) syringe pump SP2 is not activated and thus just a mixture of sample solution 6 and diluent 8 is passed to the analytical instrument 2 for analysis. After a predetermined period of time the calibration solution 7 is introduced into the sample introduction system 1 via the second syringe pump SP2. The calibration solution 7 is preferably added whilst preferably ensuring that the overall flow rate of fluid (sample solution 6, diluent 8 and calibration solution 7) into the analytical instrument 2 is maintained substantially constant.

The calibration solution 7 is preferably a standard solution comprising a number of elements at a specified concentration of, for example, 10 ppm. A multi-element solution is, for example, available from Spex Certiprep Inc. (USA) and comprises 10 μg/mL each of aluminium, arsenic, barium, beryllium, bismuth, cadmium, calcium, cesium, chromium, cobalt, copper, gallium, indium, iron, lead, lithium, magnesium, manganese, nickel, potassium, rubidium, selenium, silver, sodium, strontium, thallium, uranium, vanadium and zinc all in a solution of 5% nitric acid.

According to the preferred embodiment the flow rate of the calibration solution 7 is progressively increased whilst the flow rate of the diluent 8 is correspondingly progressively decreased whilst preferably ensuring that the total flow rate of sample 6, diluent 8 and calibration solution 7 is maintained substantially constant.

According to a less preferred embodiment the calibration solution flow rate may be progressively decreased whilst the flow rate of the diluent 8 is correspondingly progressively increased whilst again preferably ensuring that the overall flow rate of fluid into the analytical instrument 2 is maintained substantially constant.

The flow rates of the calibration solution 7 and the diluent 8 may be varied in steps or stages, or alternatively the flow rates of the calibration solution 7 and the diluent 8 may be continuously, preferably linearly, varied. Preferably, the combined flow rate of the calibration solution and the diluent is kept substantially constant.

Preferably, the flow rate of the sample solution 6 is not varied whilst the flow rates of the calibration solution 7 and diluent 8 are varied. However, according to less preferred embodiments it is contemplated that the sample flow rate could be varied whilst still preferably maintaining the overall flow rate of fluid passing to the downstream analytical instrument 2 substantially constant.

By varying the flow rates of the diluent 8 and calibration solution 7 whilst preferably leaving the flow rate of the sample solution 6 constant it is possible, in effect, to add calibration solutions of different strengths online without requiring different strength calibration solutions to be prepared offline as is required conventionally. The preferred embodiment therefore represents a considerable improvement over known calibration techniques.

The intensity of the calibration solution 7 initially added to the sample solution 6 and diluent 8 can be preset or alternatively the intensity of the calibration solution 7 added to the sample solution 6 and diluent 8 may be determined intelligently by software. For example, the data (instrument response) acquired with just the sample solution 6 and diluent 8 prior to introducing the calibration solution 7 may be integrated and the approximate concentration of the analyte in the sample solution 6 estimated using a predefined response factor. An appropriate strength calibration solution 7 can then be added which enables the concentration of the analyte(s) present in the sample solution 6 to be accurately determined.

Spikes of various different concentrations can be added to the sample solution 6 and diluent 8 as desired. Once enough data has been obtained the data can then be processed and the concentration of the analyte in the sample solution 6 accurately determined. Preferably, the concentration of the analyte of interest in the sample solution can be rapidly determined in approximately a minute, further preferably less than a minute.

FIG. 2(a) shows a preferred sample introduction system 1 in a fill mode and FIG. 2(b) shows the preferred sample introduction system in a delivery mode. The sample introduction system 1 shown in FIGS. 2(a) and 2(b) represents an improvement over the sample introduction system 1 shown and described in relation to FIG. 1 since the sample solution 6 does not get into contact with the syringe pump material thereby minimising the risk of sample contamination. The apparatus and the tubing is also easily cleanable after each experimental run thereby minimising the possibility of any memory effects. Second and further samples can also preferably be automatically loaded for subsequent analysis.

In the fill mode shown in FIG. 2(a) when the syringe pumps SP1,SP2,SP3 are respectively loading sample solution 6, diluent 8 and calibration solution 7 a peristaltic pump 5 is preferably used to maintain an approximately constant flow of fluid into the analytical instrument 2. The fluid pumped by the peristaltic pump 5 may, for example, be the same diluent 8 being loaded into the third syringe pump SP3 or it may comprise ultra pure water or other blank solutions. In the delivery mode shown in FIG. 2(b) the peristaltic pump 5 is switched OFF.

Figure 3:
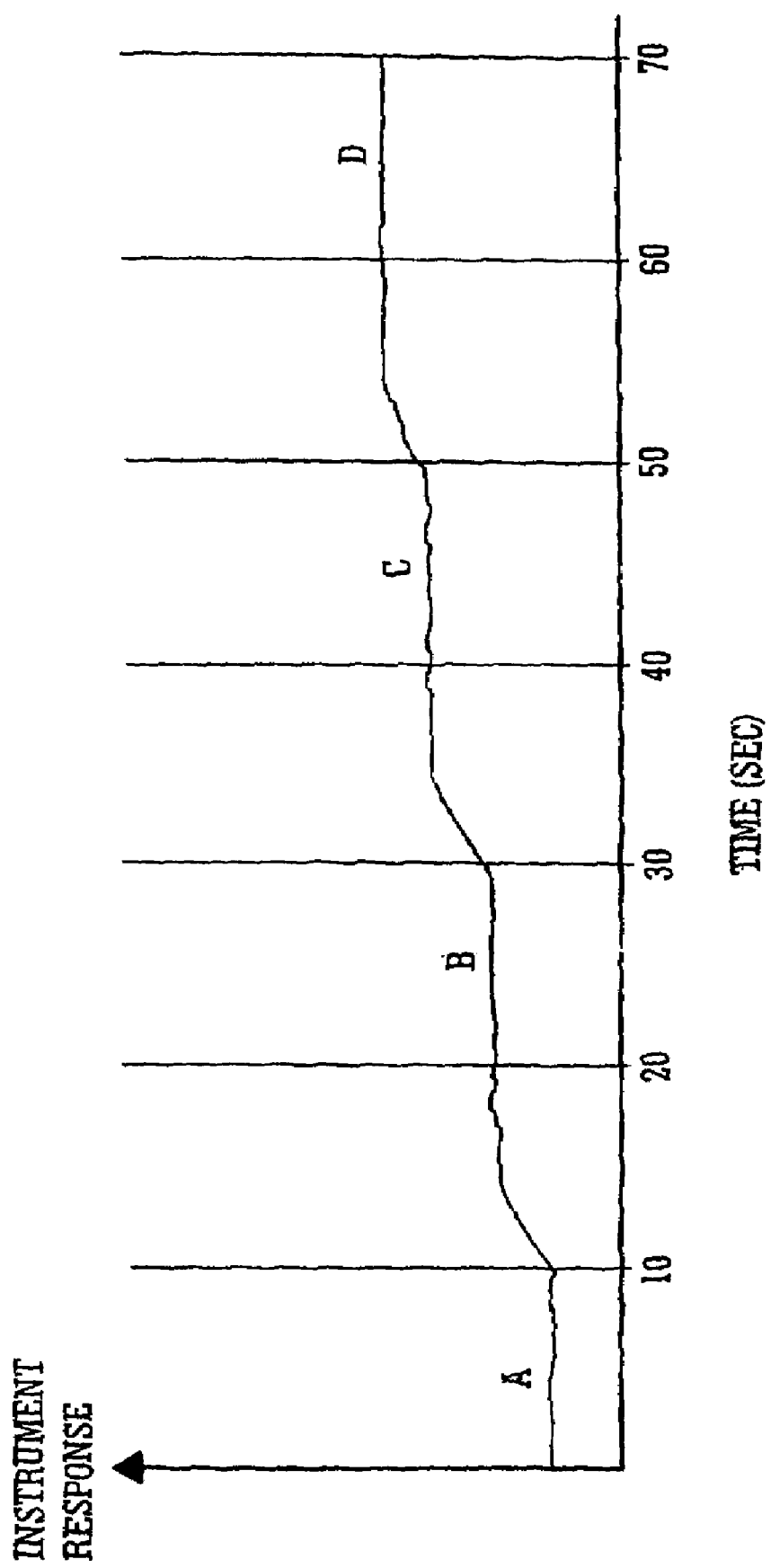
FIG. 3 shows a plot of instrument response against time when calibration solutions of increasing strength have been added to the sample.

FIG. 3 shows a typical instrument response as might be observed when using an analytical instrument 2 over an illustrative period of approximately a minute when increasingly stronger calibration solutions 7 are mixed with the sample solution 6. Response A shows the instrument response obtained when a sample solution 6 is dispensed by the first syringe pump SP1 and is mixed with a diluent 8 dispensed by the third syringe pump SP3. The sample solution 6 and diluent 8 are preferably analysed over an initial period of approximately 10 s and the approximate intensity of the analyte of interest in the sample solution 6 can be estimated.

During this first 10 s period or at the end of this period the instrument response is integrated. This enables a determination to be made of the concentrations of the calibration solution 7 which are to be subsequently introduced into the sample introduction system 1.

When the calibration solution 7 is added to the sample introduction system 1 it is preferably ensured that the overall flow rate of the sample solution 6, diluent 8 and calibration solution 7 into the analytical instrument 2 remains approximately or substantially constant. According to the preferred embodiment this is achieved by correspondingly reducing the flow rate of the diluent 8. However, according to a less preferred embodiment the calibration solution 7 can initially be introduced into the sample introduction system 1 at a relatively high level and can then be progressively reduced by progressively increasing the flow rate of the diluent 8 whilst maintaining the overall flow rate substantially constant.

After a period of approximately 10 s since a calibration solution 7 having a first concentration was introduced into the sample introduction system 1 an approximately constant signal response is obtained as shown by response B.

As shown in FIG. 3 as the calibration solution 7 or spike is added the measured intensity of the analyte of interest will be observed to increase gradually as the spike progressively reaches the detector of the analytical instrument 2. Once the response of the analytical instrument 2 has been observed to have been stable for a sufficient period of time (e.g. 10 s) allowing sufficient time for data to have been obtained, the calibration solution 7 or spike is introduced at a second concentration level and the process is repeated. Spikes of different concentrations may be added numerous times as desired (see responses C and D). FIG. 3 illustrates spikes of three different concentrations which have been added to the sample solution 6 but it is apparent that fewer or more spikes may be used. It will also be appreciated that the more spikes which are added the greater the expected accuracy of the measurement of the concentration of the analyte of interest can be determined. However, the more spikes which are added the longer the time it takes to perform an analysis.

Figure 4:
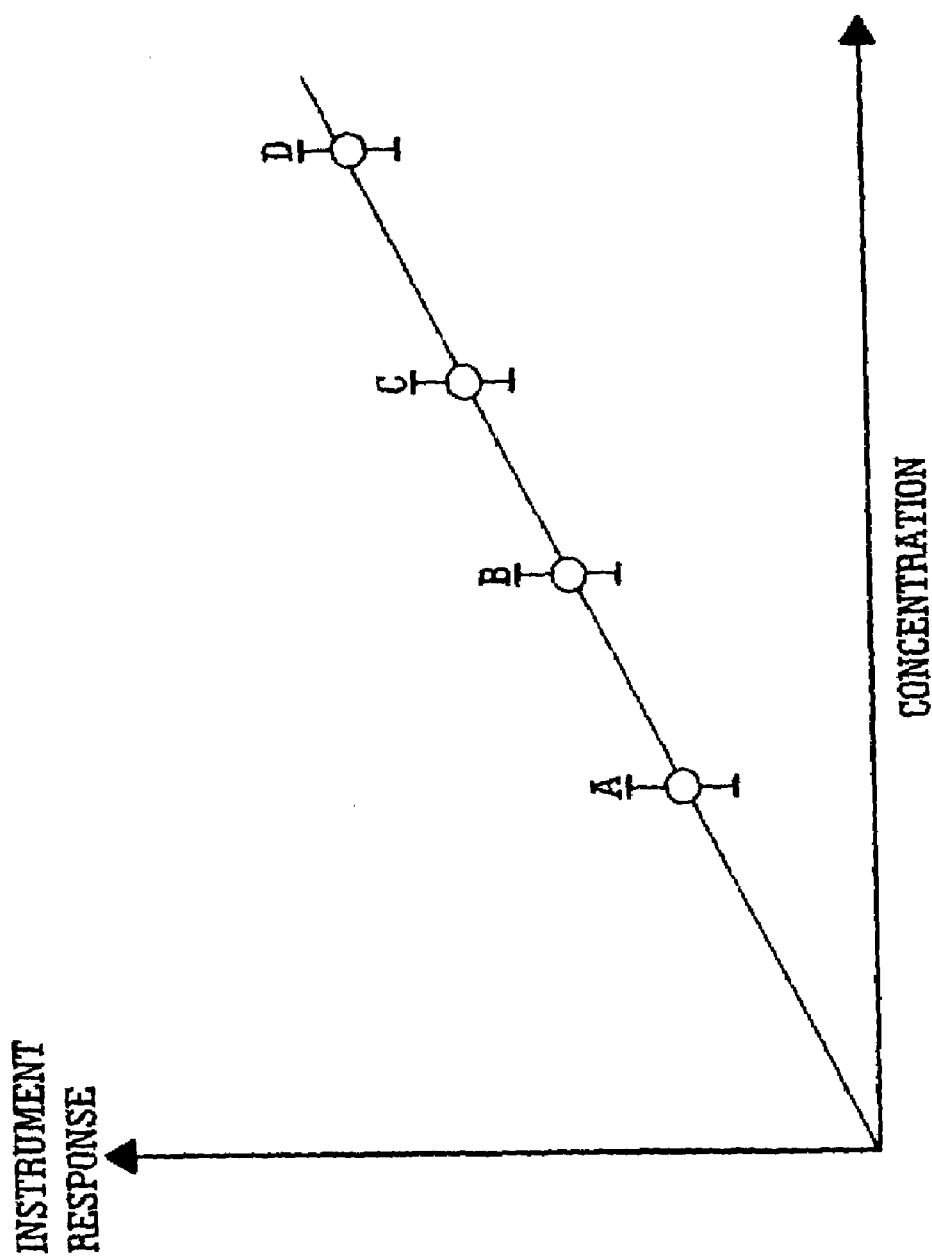
FIG. 4 shows a plot of instrument response against analyte concentration.

The instrument response A for the sample solution 6 and diluent 8 only and the sample solution 6, diluent 8 and spikes 7 of various concentration (responses B,C,D) may be plotted against the concentration of the spike to work out the actual concentration of the analyte in the sample as shown in FIG. 4. By fitting a least squares linear relationship between the response of the various data sets versus the concentration of the spike the concentration can then be determined as the ratio of the intercept over the slope of this function.

According to an embodiment of the present invention a bracketing approach may be adopted. According to this embodiment the concentration of the analyte in the sample is determined by initially introducing the sample solution 6, diluent 8 and calibration solution 7 at an initial flow rate and the instrument response is recorded. Thereafter, the flow rate of the calibration solution 7 may be increased and the flow rate of the diluent 8 correspondingly decreased so as to keep the overall flow rate substantially constant. The instrument response is again recorded. Thereafter, the flow rate of the calibration solution 7 is decreased to a flow rate below the initial flow rate with the diluent flow rate correspondingly increased so as to keep the overall flow rate substantially constant. The instrument response is then again recorded.

In otherwords, after the instrument response for the analyte has been read the system automatically injects two different concentration levels of the calibration solution 7 one to give a slightly lower reading than the initial reading and one to give a slightly higher reading than the initial reading. These standards can then be used to accurately calculate the concentration of the analyte in the sample solution 6.

It will be appreciated that although the bracketing technique has been described in relation to first increasing the calibration solution flow rate then reducing the calibration solution flow rate this sequence of steps may be reversed so that the calibration solution flow rate is at first reduced and then subsequently increased.

The bracketing technique can also be used in conjunction with external calibration and triggered only when the concentration of the sample falls outside the calibration range. Furthermore, this technique can be used to extend the dynamic range of the instrument to regions where the instrument response is not linear.

A further embodiment of the present invention is contemplated wherein only two metering pumps are used. According to this embodiment it is still possible to carry out online calibration through varying the flow of the two pumps whilst maintaining the overall flow constant. According to this embodiment one of the pumps is used to inject a sample solution having an unknown concentration of an analyte(s) of interest whilst the other pump is used to inject a calibration solution with a known concentration of the analyte(s) of interest. The concentration C of the analyte in a mixture of sample solution and calibration solution at any point in time is given by:

$$C = \frac{(C_s \cdot V_s + C_c \cdot V_c)}{(V_s + V_c)}$$

where $C_s$ is the (unknown) concentration of the analyte of interest in the sample, $V_s$ is the volume flow rate (ml/min) of the sample, $C_c$ is the known concentration of the analyte of interest in the calibration solution, and $V_c$ is the volume flow rate (ml/min) of the calibration solution. Assuming that the overall flow rate V:

$$V = V_s + V_c = \text{constant}$$

then:

$$C = \frac{C_s \cdot V_s + C_c \cdot (V - V_s)}{V}$$

$$C = \frac{V_s(C_s - C_c)}{V} + C_c$$

Assuming that the instrument response R is linearly related to the analyte concentration C in a mixture of sample solution and calibration solution, then R can be written:

$$R = m \cdot C + n$$

where m and n are the slope and the intercept of the linear relationship between R and C. Therefore:

$$R = \frac{m \cdot V_s(C_s - C_c)}{V} + m \cdot C_c + n$$

In view of the above the following sequence of measurements may be performed. Firstly, a blank solution comprising e.g. ultra pure water may be introduced into the sample introduction system (without any sample solution or calibration solution being introduced) at a flow rate V ml/minute. Then secondly, a calibration solution having a concentration $C_c$ may be introduced into the sample introduction system at the same flow rate V ml/minute without any sample solution being introduced. Then, a calibration solution having a concentration $C_c$ may be introduced in the sample introduction system at flow rate $V_2$ ml/minute together with the sample solution having a concentration $C_s$ at a flow rate $(V-V_2)$ ml/minute. The relative flow rates of the sample solution and the calibration solution may then be varied so that preferably three or four different mixtures of sample and calibration solution are introduced into the sample introduction system. It will be appreciated that the sequence of measurements described above could be performed in a different order.

The step of introducing a blank solution can be used to calculate the value of n and the step of introducing the calibration solution at the flow rate V without any sample solution can be used to calculate the value of m. The steps of providing sample solutions together with different strength calibration solutions can be used to calculate the slope of the relationship between the instrument response R and the flow rate of the sample $V_s$ and subsequently to determine $C_s$ the concentration of analyte in the sample solution.

The bracketing approach described above in relation to the embodiment having three dispensing devices may also be used in a modified form with the embodiment having only two dispensing devices.

Figure 5:
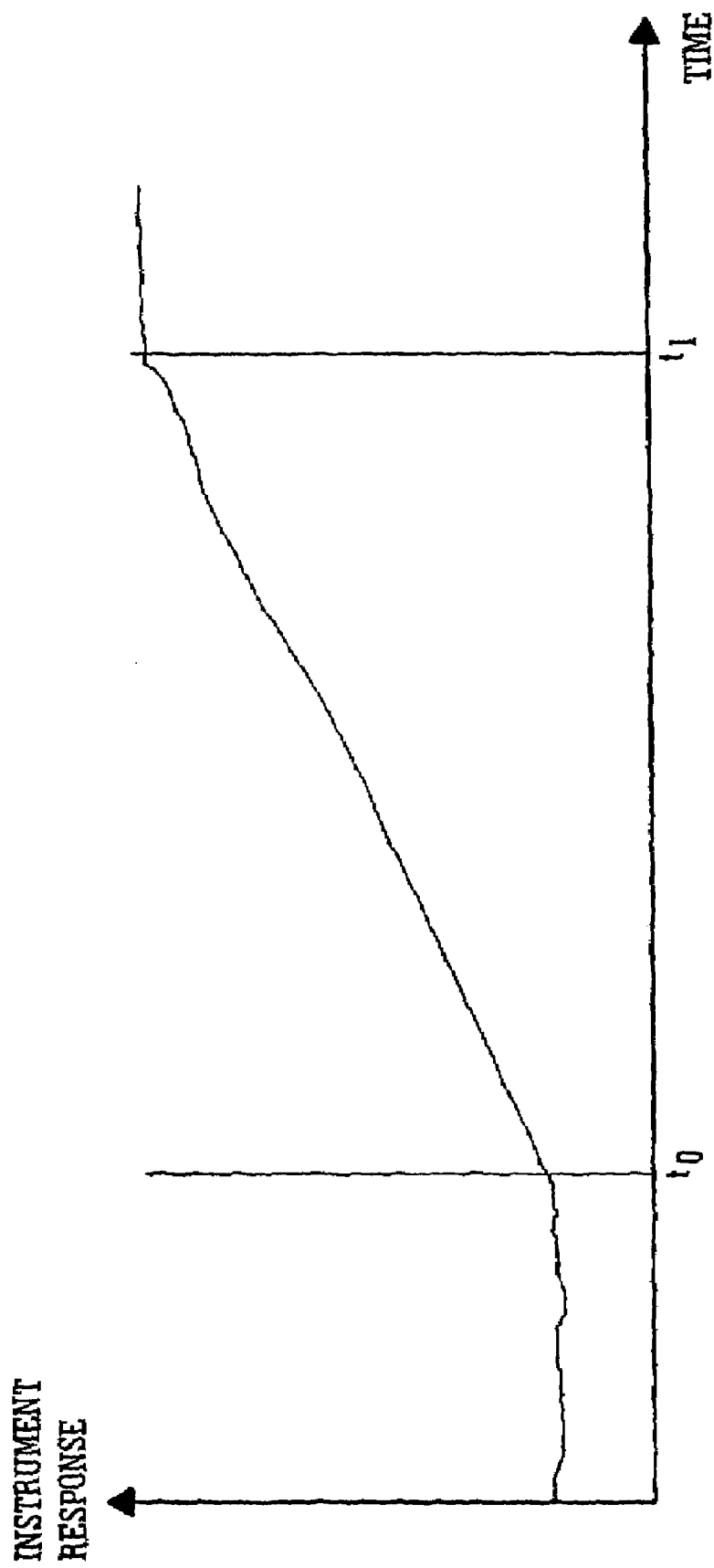
FIG. 5 shows a plot of instrument response against time according to an embodiment wherein calibration solution is continuously added to the sample.

According to the embodiment utilising three dispensing devices the flow rates of the calibration solution 7 and the diluent 8 may be continually varied (i.e. increased/decreased) whilst preferably maintaining the same overall flow rate. According to this embodiment the sample solution 6 and diluent 8 are initially input and the instrument response preferably continuously monitored. As can be seen from FIG. 5, at a time $t_0$ the flow of the diluent 8 is gradually reduced whilst at the same time the calibration solution 7 is progressively introduced. The overall flow rate of sample 6, diluent 8 and calibration solution 7 is preferably maintained constant. A real time standard addition curve similar to the one shown in FIG. 5 may be obtained. The curve enables the concentration of the analyte of interest in the sample solution 6 to be calculated in a similar manner to the approach described above in relation to FIG. 4.

Similarly, according to the embodiment utilising two dispensing devices the flow rates of the sample solution and the calibration solution may be continually varied (i.e. increased/decreased). According to these embodiments a gradient response of instrument response versus time is provided rather than a series of steps. This gradient may then be used to calibrate the response of the system.

According to both the embodiment utilising three dispensing devices and the embodiment utilising two dispensing devices the apparatus and method may be used to carry out isotope dilution procedures. In isotope dilution the sample solution is spiked with a known amount of an isotopically modified solution of known concentration and isotopic distribution which acts as an internal standard. The isotopically modified solution is used to accurately determine the concentration of analyte ions of the same element(s) as the isotopically modified solution.

The isotopically modified solution preferably comprises two or more isotopes of an element. For example, the isotopically modified solution may contain two isotopes of silver. The natural abundance of $^{107}$Ag is 51.84% and the natural abundance of $^{109}$Ag is 48.12%. The isotopically modified solution may therefore be a solution which comprises isotopically enriched silver so that there is, for example, a greater concentration of $^{109}$Ag isotopes compared with $^{107}$Ag isotopes. Knowing the amount of $^{107}$Ag and $^{109}$Ag in the calibration solution and the isotopic distribution of the calibration solution it is possible to calculate the concentration of Ag in the sample solution to a high degree of accuracy.

Figure 6:
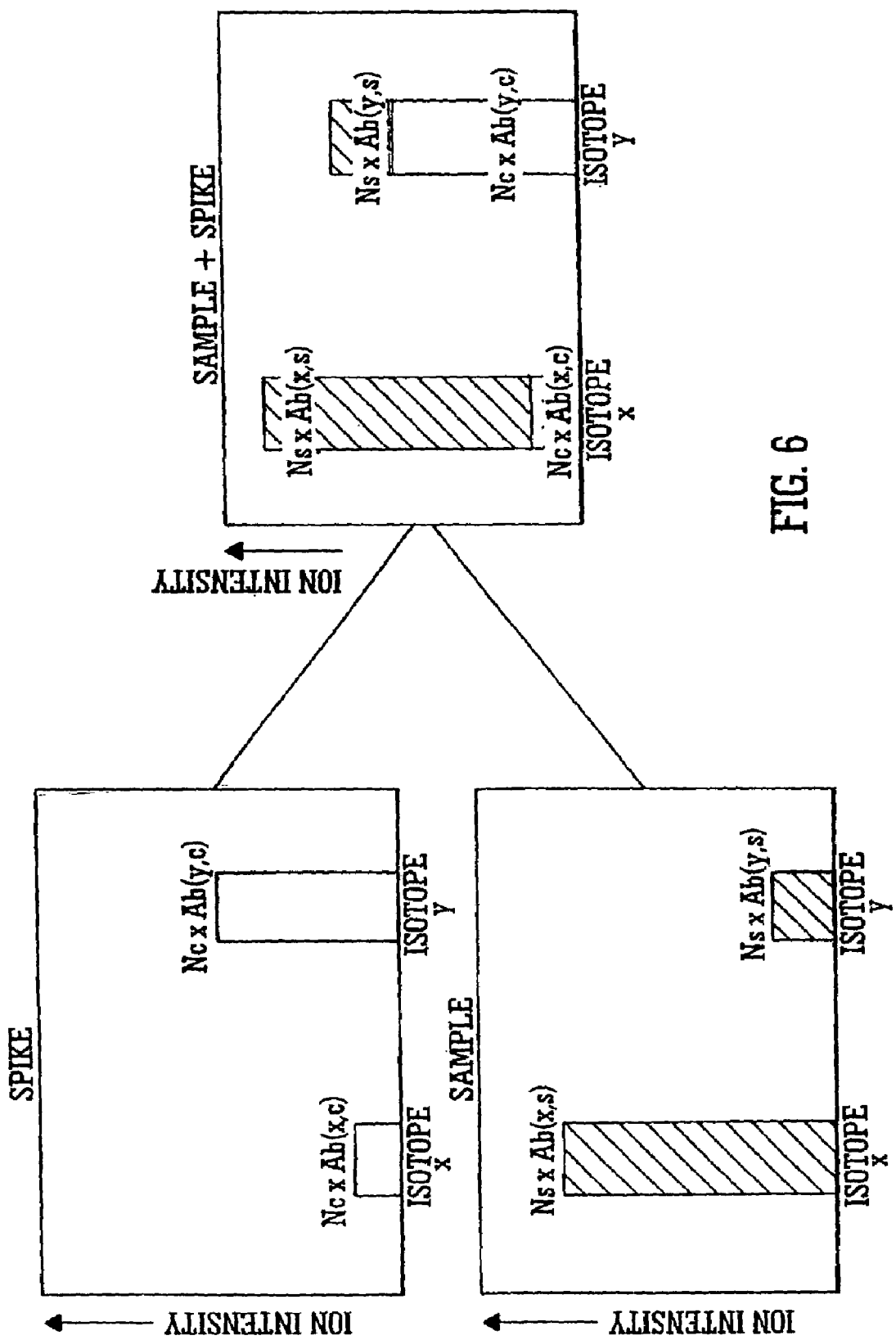
FIG. 6 illustrates the principles of isotope dilution.

With reference to FIG. 6 the ratio R of the ion intensities of isotope x over isotope y in a mixture of sample solution and calibration solution can be written as:

$$R = \frac{(N_s \times Ab_{(x,s)} + N_c \times Ab_{(x,c)})}{(N_s \times Ab_{(y,s)} + N_c \times Ab_{(y,c)})}$$

where $N_s$ is the number of analyte ions in the sample, $Ab_{(x,s)}$ is the abundance of isotope x in the sample (atoms %), $N_c$ is the number of analyte ions in the calibration solution, $Ab_{(x,c)}$ is the abundance of isotope x in the calibration solution (atoms %), $Ab_{(y,s)}$ is the abundance of isotope y in the sample (atoms %) and $Ab_{(y,c)}$ is the abundance of isotope y in the calibration solution (atoms %). This equation can be re-written as:

$$N_s = N_c \times \frac{(R \times Ab_{(y,c)} - Ab_{(x,c)})}{(Ab_{(x,s)} - R \times Ab_{(y,s)})}$$

The concentration $C_s$ of the element in the sample (g/g) can then be calculated:

$$C_s = N_s \times \frac{A_s}{6.022 \times 10^{23} \times W_s}$$

where $A_s$ is the atomic weight of the element in the sample, $W_s$ is the weight of the sample in (g) and $6.022 \times 10^{23}$ is Avogadro's number. The above equation can be re-written as:

$$C_s = 1.66 \times 10^{-24} \times \frac{A_s}{W_s} \times N_s$$

Substituting $N_s$ with the expression given above and multiplying by $10^6$ to give the concentration in (µg/g) gives:

$$C_s = 1.66 \times 10^{-18} \times \frac{A_s}{W_s} \times N_c \times \frac{(R \times Ab_{(y,c)} - Ab_{(x,c)})}{(Ab_{(x,s)} - R \times Ab_{(y,s)})}$$

Similarly, the concentration $C_c$ of the element in the calibration solution (g/g) may be written as:

$$C_c = 1.66 \times 10^{-24} \times \frac{A_c}{W_c} \times N_c$$

and in (µg/g):

$$C_c = 1.66 \times 10^{-18} \times \frac{A_c}{W_c} \times N_c$$

Therefore:

$$N_c \times 1.66 \times 10^{-18} = C_c \times \frac{W_c}{A_c}$$

and hence:

$$C_s = C_c \times \frac{A_s}{W_s} \times \frac{W_c}{A_c} \times \frac{(R \times Ab_{(y,c)} - Ab_{(x,c)})}{(Ab_{(x,s)} - R \times Ab_{(y,s)})}$$

In order to determine the concentration of an element in a sample three mass analyses are performed. Firstly, the sample is mass analysed and the intensities of the at least two isotopes of the element of interest are determined. Secondly, the solution comprising at least two isotopes of the element of interest is also mass analysed and the intensities of the at least two isotopes of the element of interest is determined. Finally, the mixture of sample and solution is mass analysed and the intensities of the at least two isotopes of the element of interest present in the mixture are analysed. From these three mass analyses the concentration of the element of interest in the sample can be accurately determined using the above equation.

Although the present invention has been described with reference to preferred embodiments, it will be understood by those skilled in the art that various changes in form and detail may be made without departing from the scope of the invention as set forth in the accompanying claims.

The invention claimed is:

1. A sample introduction system for an analytical instrument comprising:
   a first fluid including a sample with an unknown concentration $C_s$ of an analyte of interest;
   a second fluid including a calibration solution with a known concentration $C_c$ of said analyte of interest;
   a third fluid including a diluent;
   a first fluid dispensing device for dispensing the first fluid at a sample flow rate $V_s$;
   a second fluid dispensing device for dispensing the second fluid at a calibration solution flow rate $V_c$;
   a third fluid dispensing device for dispensing the third fluid at a diluent flow rate $V_d$; and
   control means for automatically varying said calibration solution and diluent flow rates wherein the control means determines the unknown concentration $C_s$ of the analyte of interest.

2. A sample introduction system as claimed in claim 1, wherein said control means is arranged to vary said calibration solution and diluent flow rates whilst maintaining a sum of said sample flow rate, said calibration solution flow rate and said diluent flow rate at a substantially constant value V.

3. A sample introduction system as claimed in claim 2, wherein said control means increases said calibration solution flow rate and decreases said diluent flow rate.

4. A sample introduction system as claimed in claim 3, wherein said control means increases said calibration solution flow rate and decreases said diluent flow rate in steps.

5. A sample introduction system as claimed in claim 3, wherein said control means continuously increases said calibration solution flow rate whilst simultaneously continuously decreasing said diluent flow rate.

6. A sample introduction system as claimed in claim 2, wherein said control means decreases said calibration solution flow rate and increases said diluent flow rate.

7. A sample introduction system as claimed in claim 6, wherein said control means decreases said calibration solution flow rate and increases said diluent flow rate in steps.

8. A sample introduction system as claimed in claim 6, wherein said control means continuously decreases said calibration solution flow rate whilst simultaneously continuously increasing said diluent flow rate.

9. A sample introduction system as claimed in claim 1, further comprising a mixing device for mixing first fluid dispensed from said first dispensing device with third fluid dispensed from said third dispensing device.

10. A sample introduction system as claimed in claim 9, further comprising a further mixing device for mixing a mixture of first and third fluids with second fluid dispensed from said second dispensing device.

11. A sample introduction system as claimed in claim 1, wherein said diluent has substantially a 0% concentration of said analyte of interest.

12. A sample introduction system as claimed in claim 1, wherein said first, second and third dispensing devices comprise syringe pumps.

13. A sample introduction system as claimed in claim 1, in combination with a mass spectrometer, wherein said sample introduction system is arranged to introduce a sample to an ion source of the mass spectrometer.

14. An analytical instrument comprising:
a sample introduction system including:
a first fluid including a sample with an unknown concentration $C_s$ of an analyte of interest;
a second fluid including a calibration solution with a known concentration $C_c$ of said analyte of interest;
a third fluid including a diluent;
   a first fluid dispensing device for dispensing the first fluid at a sample flow rate $V_s$;
   a second fluid dispensing device for dispensing the second fluid at a calibration solution flow rate $V_c$;
   a third fluid dispensing device for dispensing the third fluid at a diluent flow rate $V_d$; and
   control means for automatically varying said calibration solution and diluent flow rates, wherein the control means determines the unknown concentration $C_s$ of the analyte of interest.

15. An analytical instrument as claimed in claim 14, wherein said analytical instrument is selected from the group consisting of: (i) an Inductively Coupled Plasma ("ICP") mass spectrometer; (ii) an Inductively Coupled Plasma optical analyser; (iii) a flame spectrophotometer; (iv) an Atmospheric Pressure Chemical Ionisation ("APCI") mass spectrometer; and (v) an Electrospray Ionisation ("ESI") mass spectrometer.

* * * * *